(12) United States Patent  
Kask

(10) Patent No.: US 6,515,289 B1  
(45) Date of Patent: *Feb. 4, 2003

(54) METHOD FOR CHARACTERIZING SAMPLES ON THE BASIS OF INTERMEDIATE STATISTICAL DATA

(75) Inventor: Peet Kask, Harku (EE)

(73) Assignee: Evotec Biosystems AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/445,428

(22) PCT Filed: Jun. 10, 1998

(86) PCT No.: PCT/EP98/03509

§ 371 (c)(1),  
(2), (4) Date: Dec. 10, 1999

(87) PCT Pub. No.: WO98/57150

PCT Pub. Date: Dec. 17, 1998

(30) Foreign Application Priority Data

Jun. 10, 1997 (EP) .............................. 97109353

(51) Int. Cl.$^7$ ................................................ G01N 21/64
(52) U.S. Cl. ...................................................... 250/459.1
(58) Field of Search .......................... 250/458.1, 459.1, 250/461.1, 461.2

(56) References Cited

U.S. PATENT DOCUMENTS

| | | | | |
|---|---|---|---|---|
| 3,824,402 A | | 7/1974 | Mullaney et al. ........... 250/565 |
| 4,676,641 A | * | 6/1987 | Bott ........................... 356/336 |
| 5,294,799 A | | 3/1994 | Aslund et al. ........... 250/458.1 |
| 5,382,789 A | * | 1/1995 | Aoshima ..................... 250/216 |
| 5,410,030 A | * | 4/1995 | Yue et al. .................. 536/23.1 |
| 5,442,045 A | * | 8/1995 | Haugland et al. ........ 530/391.3 |
| 5,627,642 A | | 5/1997 | Dhadwal et al. ............ 356/336 |
| 5,912,137 A | * | 6/1999 | Tsien et al. ................... 435/15 |
| 6,204,068 B1 | * | 3/2001 | Soini et al. ................. 436/518 |
| 6,208,815 B1 | * | 3/2001 | Seidel et al. ................ 396/337 |

FOREIGN PATENT DOCUMENTS

| | | |
|---|---|---|
| DE | 43-01-005 A | 7/1994 |
| DE | 44-38-391 A | 5/1996 |
| EP | 0-359-681 | 3/1990 |
| EP | 0-590-775 A | 4/1994 |
| EP | 0-762-114 A | 3/1997 |

* cited by examiner

*Primary Examiner*—Constantine Hannaher  
*Assistant Examiner*—Shun Lee  
(74) *Attorney, Agent, or Firm*—Jacobson Holman PLLC

(57) ABSTRACT

A method for characterizing a sample involves: a) monitoring the sample for intensity fluctuations of radiation emitted, scattered and/or reflected by units of the sample in at least one measurement volume with at least one detector which is able to detect radiation emitted, scattered and/or reflected by the units, b) determining from the intensity fluctuations intermediate statistical data of an at least two-dimensional joint statistical function, and c) determining information related to a joint distribution of the units out of the intermediate statistical data.

89 Claims, 13 Drawing Sheets

METHOD FOR CHARACTERIZING SAMPLES ON THE BASIS OF INTERMEDIATE STATISTICAL DATA

The present invention relates to a method for characterizing samples on the basis of intermediate statistical data.

The essence of a number of pharmacological, biological and chemical problems is to detect substances in a sample or to measure the interaction or reaction of these substances. In order to measure the substances in a sample more specifically, usually at least one of the reactants is radioactively or luminescently labelled. A convenient and sensitive type of labels are fluorescent labels.

Widely used methods to monitor interactions by fluorescence are the determination of changes in overall fluorescence intensity or in anisotropy of fluorescence. However, a number of side effects, such as surface binding or fluorescence from impurities, often lead to interpretation problems and artifacts. A second reason which has induced interest towards refined methods of analysis is the need to work with small amounts of a large number of samples in the field of high throughput screening and large capacity diagnostics.

New opportunities for assay development were opened when the technology for monitoring fluorescence from single fluorophore molecules became available. The first successful studies on fluorescence intensity fluctuations were performed by Magde, Elson and Webb (Biopolymers, Vol. 13, 29–61, 1974) who demonstrated the possibility to detect number fluctuations of fluorescent molecules and established a research field called fluorescence correlation spectroscopy (FCS). FCS was primarily developed as a method for determining chemical kinetic constants and diffusion coefficients. The experiment consists essentially in measuring the variation of the number of molecules of specific reactants in time in a defined open volume of solution. Microscopic fluctuations of the concentration of the reactant are detected as fluorescence intensity fluctuations from a small, open measurement volume. The measurement volume is defined by a focussed laser beam, which excites the fluorescence, and a pinhole in the image plane of the microscope collecting fluorescence. Intensity of fluorescence emission fluctuates in proportion with the changes in the number of fluorescent molecules as they diffuse into and out of the measurement volume and as they are created or eliminated by the chemical reactions. Technically, the direct outcome of an FCS experiment is the calculated autocorrelation function of the measured fluorescence intensity.

An important application of FCS is to determine concentrations of fluorescent species having different diffusion rates in a mixture. In order to separate the two terms corresponding to translation diffusion of two kinds of particles in the autocorrelation function of the fluorescence intensity, at least about a two-fold difference in diffusion time is needed, which corresponds generally to an eight-fold difference in the mass of the particles. Furthermore, if one succeeds in separating the two terms in the autocorrelation function of fluorescence intensity, it is yet not sufficient for determining the corresponding concentrations except if one knows the relative brightness of the two different types of particles.

The international patent application WO-A-98/16814 describes a method for characterizing samples by measuring a number of photon counts emitted, scattered and/or reflected by units in said sample in a repetitive mode per time interval of defined length, and determining a function of the number of photon counts per said time interval, characterized in that a function of specific brightness of said units is determined on basis of said function of the number of photon counts. This method can also be applied to study fluorescent samples. This special embodiment is the so called fluorescence intensity distribution analysis (FIDA). While FCS distinguishes between different species according to their diffusion time, FIDA distinguishes between them according to their specific brightness. Both FCS and FIDA rely on a single specific physical property. In principle, however, one-dimensional statistical functions obtained by FCS or FIDA can be used for determining distributions of particles in more than one specific physical property (e.g. distribution of particles according to both translational and rotational diffusion coefficient), but this option is limited and may be of low reliability.

The European patent application EP-A-0 359 681 discloses modulated dynamic light scattering methods which utilize time and space modulations of the incident or scattered light as well as modulations caused by random Brownian motions of the particles to measure particular properties.

A further method which utilizes fluorescence is Fluorescence Analysis in Cell Sorting (FACS). In FACS machines, the intensity of light emitted by a single particle is measured with a relatively high precision, and intensities corresponding to different wavelengths, scattering or polarization angles can be plotted simultaneously. U.S. Pat. No. 3,824,402 to Mullaney et al. discloses such a photometric apparatus and method for measuring light responsive characteristics of appropriately stained biological cells. At least two light responsive characteristics are measured and compared to eliminate spurious light induced noise. More particularly, light scattering produced by the cells and fluorescent light emitted by the cells in response to an incident light beam are detected. However, ordinary FACS cannot be applied in cases when the particles under study arrive and leave the measurement volume at random pathways, so that a lot of them do not pass through the centre of the focus. Also, the set of procedures used in FACS is not applicable in cases when light intensity corresponding to individual particles is so weak that the stochastical error of its measurement exceeds differences in intensities corresponding to different species of particles. Furthermore, FACS is applicable only at extremely low concentrations of particles, corresponding to much less than one particle per measurement volume.

One object of the invention is to increase the reliability of analysis of samples and reduce risk of misinterpretation of the measured data.

Another object of the invention is to considerably broaden the field of applicability of multidimensional analysis of samples.

The objects of the present invention are solved with the method having the features of characterizing samples which contain fluorescent molecules or particles, comprising the steps of:

a) monitoring intensity fluctuations of radiation emitted by the molecules or particles in at least one measurement volume by detecting sequences of photon counts by a single, two or more photon detectors, b) determining from a probability function of at least two arguments, wherein at least one of the arguments is a number of photon counts $n_1$ counted by detector 1 and another argument is a number of photon counts $n_2$ counted by detector 2, c) determining a distribution of molecules or particles as a function of at least two specific physical properties out of said intermediate statisical data.

Figure 1:
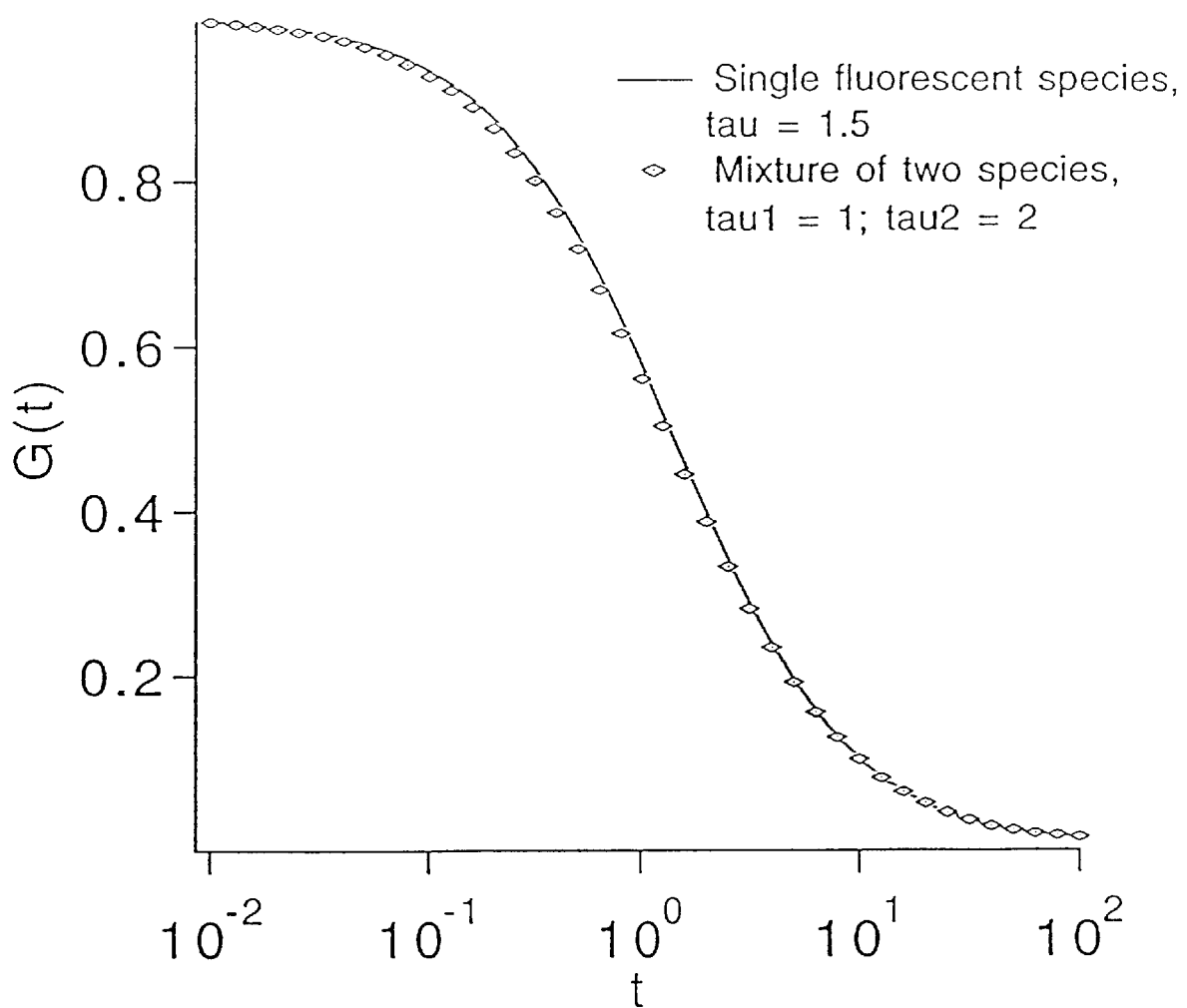
FIG. 1. is a graphic illustration of the ability of FCS to analyze mixtures as a correlation function G(t) calculated for a mixture of two species.

It is to be understood that the following description is intended to be illustrative and not restrictive. Many embodiments will be apparent to those of skill in the art upon reviewing the following description. By way of example, the invention will be described primarily with reference to monitoring numbers of photon counts from light emitted by fluorescently labelled particles in a sample. This is because fluorescence is a very sensitive means allowing to monitor single molecules, and still rather selective allowing to distinguish between different species. However, in some embodiments it may be desirable to monitor numbers of photon counts of other origin than fluorescence.

The term "unit of a sample" refers, in general, to subparts of a sample which are capable of emitting, scattering and/or reflecting radiation. A sample might contain a number of identical units or different units which preferably can be grouped into species. The term "different species" refers also to different states, in particular different conformational states, of a unit such as a molecule. Fluorescently labelled or naturally fluorescent molecules, molecular complexes, vesicles, cells, beads and other particles in water or other liquids may be examples of fluorescent units in liquid samples, while examples of fluorescent units of a solid sample are impurity molecules, atoms or ions, or other fluorescence centers.

What is meant by the term "specific physical property" is generally a physical measurable property having a certain value or interval of values or distribution of values for one species and, in general, another value or interval of values or distribution of values for another species. Examples of specific physical properties are: diffusion coefficient, absorption cross-section, quantum yield of fluorescence, specific brightness, anisotropy of fluorescence, fluorescence decay time, ratio of fluorescence intensity passing through different optical filters, etc.

The specific brightness in the sense of the present invention is a physical characteristic which expresses in what extent a unit of given species is able to emit, scatter and/or reflect radiation. It is thought to characterize single units and therefore the value of specific brightness is neither depending on concentration of the units, nor on the presence of other units. Thus, a change of the total count rate of photons emitted, scattered and/or reflected from the measurement volume, if only due to a change in concentration of the total number of units, does not influence the value of specific brightness. Specific brightness of a unit is usually expressed in terms of the mean count rate per unit which is a weighted average of the count rate over coordinates of the unit in the measurement volume.

What is meant by the term "at least two-dimensional joint statistical function" is a function of two or more arguments which can be determined from sequences of photon counts detected by a single, two or more photon detectors. The adjective "statistical" means that the function is determined as an average over time or realizations, while its expectation is thought to be a non-trivial function, expressing sensitive information about the sample. The adjective "joint" is meant to denote that the multidimensional statistical function can be generated out of a sequence or group of sequences of photon counts without the requirement to generate at least one one-dimensional statistical function for each of several separately detected sequences or groups of sequences of photon counts and assemble the multidimensional statistical function out of these one-dimensional functions. Separately detected is meant to denote that the sequence or groups of sequences of photon counts are detected with separate detectors or groups of detectors, respectively, or detected by the same detector or group of detectors, respectively, in consecutive measurements. For example, if a correlation function of light intensity is determined at different conditions (e.g. at different angles of a polarization cube), then the resulting two-dimensional function G (t, α) (with its arguments delay time and angle) is considered not to be a joint statistical function, while the probability p ($n_1, n_2$) to count $n_1$ photons by detector 1 and $n_2$ photons by detector 2 is a typical example for a joint statistical function. Other examples of intermediate two-dimensional joint statistical functions are as follows: number of events versus number of counts and time delay from an incident count; two-dimensional Fourier spectrum of the photon detection function by two photon detectors; two-dimensional moments of the two-dimensional joint distribution of the number of photon counts; probability versus number of photon counts in a counting time interval and (versus) width of counting time interval p (n, T). Correlation function and distribution function may be regarded as seeds for a number of different types of multidimensional joint statistical functions, mathematical transformations being responsible for their great variety.

The importance of the present invention for the characterization of samples may be illustrated by the following, non-limiting example: Assuming that a solution contains relatively small labelled ligand molecules and beads bearing two receptors, then one has to distinguish between three fluorescent species: free ligand molecule (L), one ligand molecule bound to a bead (BL), and two ligand molecules bound to a bead (BLL). The assumption is made that no quenching of fluorescence occurs upon binding.

FCS would separate at best two terms: the first with the diffusion time of L, and the second with the diffusion time of both BL and BLL, which are practically equal because the bead has a much larger molecular weight than the ligand. The outcome of FIDA would be two values of specific brightness: that of BLL being two times higher than that of BL or L. The conclusion of these analyses could be that the sample contains two species, and in case of about 1:1 ratio of amplitudes, one could not decide which value of the diffusion time corresponds to which value of the specific brightness.

The method of the present invention, however, can be applied to distinguish all three species, because they differ between each other in at least one out of the two specific properties of analysis.

According to the invention, a new quality of characterization of samples containing units which emit, scatter and/or reflect radiation becomes possible. In the first step, intensity fluctuations of radiation emitted, scattered and/or reflected by units in at least one measurement volume are monitored with at least one detection means which is capable to detect said radiation. In a second step of the method according to the invention, intermediate statistical data comprising an at least two-dimensional joint statistical function are determined from the detected intensity fluctuations. It might be preferred to additionally consider other data than the joint statistical function as part of the intermediate statistical data set. In particular, it might be preferred that said intermediate statistical data additionally comprise one-dimensional statistical functions. In a third step, information related to a joint distribution of units is determined out of said intermediate statistical data.

An important step of the method according to the invention is the determination of a set of intermediate statistical data, comprising at least one at least two-dimensional joint statistical function, out of the measured stochastical data of radiation intensity fluctuations. Which set of intermediate data is to be determined depends on the specific physical properties of interest. If the diffusion coefficient and the specific brightness are chosen as the two specific properties to distinguish between different species in the sample, then the two-dimensional joint statistical function has to depend somehow both on specific brightness of said species and the speed at which the species enter and leave the measurement volume. In this particular case, a suitable selection is p (n, k) which is the conditional probability to count n photons in the k-th time interval provided an occasional photon of incidence was counted in the 0-th time interval. Other selections are also possible, as for example p (n, T) which is the probability distribution of the number of counts as a function of the width of the counting time interval.

Another example is the characterization of samples on basis of the two specific brightnesses corresponding to parallel and perpendicular polarizations. (It should be noted that different species differ not only by brightness of fluorescence, but also by anisotropy of polarization, i.e. by ratio of the two brightnesses.) In this case, it is adequate to use two detection means, one for the parallel and the other for the perpendicular polarization. As an intermediate statistical data set, one can select p ($n_1$, $n_2$) which is the joint probability to count $n_1$ photons by the detection means for parallel polarization and $n_2$ photons by the other detection means during the same counting interval. From the joint distribution p ($n_1$, $n_2$), one can determine characteristic polarization ratios for two or more fluorescent species at a time without the need to prepare and measure solutions of single species which is often difficult or even impossible.

In a preferred embodiment, the fluctuating intensity of radiation is monitored in terms of determining numbers of photon counts in, preferably consecutive, time intervals of given length. In a further preferred embodiment, said intensity fluctuations of radiation are monitored in terms of determining time of arrival of photons and/or length of time intervals between a given number of consecutive photon counts.

It might be preferred to select intermediate statistical data from a group consisting of unconditional and conditional distributions of the number of photon counts, distributions of time intervals between consecutive photon counts, autocorrelation functions, cross-correlation functions, and combinations thereof.

At least one of the arguments of the joint statistical function might be time. In another embodiment, at least one of the arguments of said joint statistical function is the number of photon counts in time intervals of given length or length of time intervals between a given number of consecutive photon counts. It might further be preferred that at least one of the arguments belongs to the class of arguments of mathematical transforms of either probability or correlation functions.

It might be preferred to determine in step c) the presence or absence or concentration of at least one unit or species of units with a specific combination of at least two physical properties. At least two species might be separated based on at least two physical properties.

It might also be preferred to include into the method the separation of at least one species from any background influence based on at least one physical property and/or to derive at least one one-dimensional statistic after performing a separating operation based on at least one physical property.

With regard to step c) in a further embodiment, a joint distribution of units as a function of at least two specific physical properties is determined out of said intermediate statistical data.

According to a further embodiment, the intermediate statistical data in step b) are derived from the intensity fluctuations directly or from fluctuations of local statistical functions of intensity.

According to a further preferred embodiment, the units are particles, molecules, aggregates, vesicles, cells, viruses, bacteria, centers, or mixtures thereof in solids, liquids or gases. It might be preferred to group units into species which can be distinguished by at least one of their specific physical properties. At least one of the species can be luminescent, preferably fluorescent, and/or can be luminescently labelled.

It might be preferred to monitor the intensity fluctuations of fluorescence with the help of only one detection means. If one is interested in characterization of species according to more than one specific brightness corresponding, for example, to different polarizations or spectral sensitivities of fluorescence detection, then it might be preferred to use more than one detection means. Any detector which is capable to detect radiation emitted, scattered and/or reflected by units of the sample may be used. Appropriate detection means such as an avalanche photo-diode, a photomultipier or conventional photodiodes are well known to those of skill in the art. It might also be preferred to use a multidetector consisting of a monolithic configuration of a plurality of detectors, especially if one wants to measure a set of samples in parallel as it is the case in miniaturized high throughput screening. It might further be preferred to use a two-dimensional multiarray detector.

In one preferred embodiment, at least one of the specific physical properties characterizing said units is the diffusion coefficient, or correlation time of radiation intensity fluctuations, or any other property expressing how fast or slow Brownian motion of given units is.

In a further preferred embodiment, at least one of the specific physical properties characterizing a unit is the specific brightness. More details about the determination of specific brightness as well as applications are disclosed in U.S. patent application Ser. No. 09/029,830 which is herein incorporated by reference.

It may further be preferred that at least one of the specific physical properties characterizing fluorescent units is the polarization ratio of their fluorescence, or fluorescence anisotropy, or any other property expressing the extent of polarization of fluorescence. For example, a solution of two fluorescent species is described not only by the polarization ratio of fluorescence of the whole sample, but also by two specific polarization ratios characterizing the two species. Usually, these last two properties are determined by studying fluorescence of pure solutions of given species. According to the present invention, these properties can also be determined from monitoring fluorescence intensity fluctuations of the mixture of said species.

In one embodiment, at least one of the specific physical properties characterizing the fluorescent units is the ratio of fluorescence intensities corresponding to different excitation wavelengths and/or different spectral sensitivities of fluorescence detection, or any other property expressing the dependence of fluorescence intensity on the wavelength of excitation and/or detection.

In a preferred embodiment, at least one of the specific physical properties characterizing said fluorescent units is lifetime of fluorescence.

The specific physical properties, in particular luminescence properties like fluorescence lifetime or fluorescence anisotropy, of the units can be varied by conjugating them with a specific luminophore via different linker molecules. It may be preferred to use polymeric linker molecules consisting of a varying number of equal or different monomers.

The luminescence properties of the units may also be varied by conjugating them with a first molecule, as e.g. biotin, which binds a luminescently labelled second molecule, as e.g. luminescently labelled avidin or streptavidin.

The luminescence properties of a unit can also be changed by energy transfer. Energy absorbed by a donor unit is transferred upon close contact to a luminophore of an acceptor unit and subsequently emitted.

The method according to the present invention is particularly well suited for high throughput screening, diagnostic purposes, monitoring polymerization, aggregation or degradation processes, for particle sorting, nucleic acid sequencing, or for general analytical purposes, such as environmental analytics or process control.

In screening procedures, substances that are possibly pharmacologically active can be analyzed through their interaction with specific receptors by examining said interaction with binding of a luminescently labelled ligand to receptors wherein natural receptors on their carrier cells as well as receptors on receptor-overexpressing carrier cells or receptors on vesicles or receptors in the form of expressed molecules or molecular complexes may be used. Moreover, the interaction of substances with enzymes in solution or in their genuine cellular environment can be detected by monitoring a change of the substrate of the enzyme, e.g. a change in size, brightness, rotational diffusion, or any other of the above mentioned fluorescence properties. Another means of determining enzyme activity is to add a fluorescently labelled molecule, which binds to either educt or product of the enzymatic reaction. Another method for investigating pharmacological activity of substances is the measurement of reporter systems such as Green Fluorescent Protein (GFP) expresssion, and of the properties of molecules to which GFP is attached. Further applications, especially concerning the performance of assays, are disclosed in WO-A-94/16313 (herein incorporated by reference).

For the detection of specific recognition reactions, potential active substances can be present in complex natural, synthetic or semisynthetic mixtures which are subjected to separation prior to analysis. These mixtures can be separated first e.g. by chromatography to test the individual fractions for the presence of functional compounds preferably "on line" in a capillary at the end of a separation matrix. The coupling of fractionating methods with FCS detection is described in detail in WO-A-94/16313 (herein incorporated by reference).

With respect to the determination of interactions between antigens and antibodies, the antigen is often presented in a crude biological matrix which may be a source of high background signals such as autofluorescence, or can otherwise distort the "pure" signal, e.g. by absorption of fluorescence photons or unspecific binding of the labelled probe to other particles of the sample. By identifying the antigen-antibody complexes via, for example, the size of the molecular complex and its brightness, they can be separated from the signal caused by artifacts.

Another task in diagnostics is to identify nucleic acid strands by a labelled probe molecule, such as an specific oligomer. With the use of a primer "cocktail", which e.g. can exist of primers labelled with dyes of different brightness, a target nucleic acid can be identified by the diffusion time and the number of primers having bound to it. A method for direct identification of few nucleic acid strands with a primer cocktail, which preferably consists of a mixture of different, short primers each with a so-called antisense-sequence complementary to a section of the target molecule and marked with one or more dye molecules, is disclosed in DE-A-195 08 366 (herein incorporated by reference).

Often, aggregation and degradation are phenomena to be monitored. Aggregates display brightnesses and diffusion times different from the monomers. In determining both properties, the measurements become more precise and do not exhibit a bias due to different molecular brightnesses, as it would be the case with FCS alone.

In sequencing according to the method of Sanger, oligomers of different length, of which the terminating nucleic acid is labelled with a dye, are identified. Advanced techniques, as e.g. the one described in DE-A-38 07 975, use dyes which exhibit different properties, such as fluorescence lifetime, according to the type of base they are attached to. The determination of a base is much more secure if several properties, such as fluorescence lifetime and brightness, or any other specific physical property, are determined according to the invention and cross checked for consistency. In a preferred embodiment, the sample to be sequenced is separated by gel or capillary electrophoresis, or a separation step is conducted by capillary electrochromatography, electrohydrodynamic migration or related electrokinetic methods.

In particle sorting, especially in cell or bead sorting, the task is to separate cells or beads according to their biological or chemical properties which can be monitored by their fluorescence properties. Prior state of the art just monitors fluorescence intensity or intensity of scattered light in a measurement volume much larger than the size of the cell or of comparable size to the bead. Thus, cells or beads binding only partly a ligand which is also present unbound in the surrounding solution cannot be monitored by prior art. The current invention solves this problem even for relatively large measurement volumes by determining fluorescence and/or molecular parameters different from mere intensity, and thus enables the separation of both contributions, that of the bound and the one of the unbound ligand.

The importance of the present invention for the characterization of samples may be further illustrated by the following, non-limiting example: Assuming that a solution contains relatively small luminescent ligand molecules which tend to form aggregates as well as beads with multiple binding sites for these luminescent ligand molecules. Then one might want to distinguish between aggregates of a particular number of luminescent ligand molecules (A) and beads to which the same number of luminescent ligand molecules is bound (B). The two-dimensional analysis according to the present invention allows distinguishing species A, which is a fast diffusing component with a specific brightness, from species B, which is a slower diffusing component with the same specific brightness as A.

In one embodiment, said intermediate statistical data are fitted using a priori information on said sample. In a further embodiment, said statistical data are processed applying multidimensional inverse transformation with linear regularization (ITR) or inverse transformation with constraints (ITC) or inverse transformation with regularization and constraints (ITRC). Inverse transformation can be used to determine which composition of the sample would yield the theoretical values of the intermediate statistical data set closest to the experimental data. Because of statistical errors and limited sizes of measured data, inverse transformation is often an ill-posed mathematical problem, characterized by wild oscillations in its outcome. ITR, ITC and ITRC stabilize the mathematical problem by looking for a "regular" (e.g. a smooth) or constrained solution, for example by minimizing the sum of squared deviations of statistical data and a function of the solution itself, penalizing "irregular", usually irreproducible structures in the outcome, or values having no physical meaning. An example of constraining is disallowing negative values for concentrations. (For the method of ITR, see, e.g., W. H. Press, S. A. Teukolsky, W. T. Vetterling, B. P. Flannery, Numerical recipes in C: the art of scientific computing, second edition, Cambridge University Press, 1992, p. 808).

In a preferred embodiment, the measurement volume is only a part of the total volume of the sample and said units are diffusing and/or being actively transported into and out of said measurement volume and/or said sample is actively transported and/or optically scanned. If said units, e.g. fluorescent particles, are sufficiently small, then diffusion is fast enough for data acquisition from a great number of counting intervals. However, if the characteristic time of diffusion is substantially longer than the time interval for measuring fluorescence intensity, then active transport (flow or scanning) can considerably save time of data acquisition.

In fluorescence studies, it may be advantageous to take measures for reducing the background count rate, arising from Raman scattering in the solute material and dark count rate of the detector, with respect to the count rate per unit. In particular, it is in some cases preferred to use measurement volumes smaller than $10^{-12}$ l, more preferably smaller than $10^{-14}$ l.

The measurement volumes can preferably be arranged on two-dimensional carriers, such as membranes or sheets having wells. Suitable carrier systems are described in WO-A-94/16313 as well as in the German patent application DE-A-196 53 766.5.

The latter discloses a polymeric disk with multiple wells. In particular, this disk has dimensions of known compact discs (CD) or mini CDs.

Advantageously, the high signal to background count rate and the small optical measurement volume may be achieved by using at least one microscope objective, preferably with a numerical aperture $\geq 0.9$, in a confocal manner for both focussing the incident laser beam and collecting radiation emitted, scattered and/or reflected by units in said sample. A suitable device is disclosed in WO-A-94/16313 (herein incorporated by reference).

In a further preferred embodiment, the measurement volume is restricted by the use of elements of near field optical microscopy. Near field optical microscopy means here that the light passes through an aperture with at least one of its dimensions being smaller than the wavelength of the light used and which is in direct contact to the measurement volume. The aperture may consist of an opaque layer with at least one hole of said diameter or at least one slit of appropriate width and/or a tapered glass fiber or wave guide with a tip diameter of said width, optionally coated with an opaque layer outside. Near field optical microscopy can be used for focussing the excitation light of the units, and/or collecting the light emitted by the units. A suitable device is disclosed in WO-A-96/13744 (herein incorporated by reference).

Another preferred embodiment combines near field optical microscopy for the excitation light path, and conventional optical microscopy for the emission light path, or vice versa. The present invention profits from such a realization in the sense that the size of the measurement volume is reduced compared to conventional confocal microscopy. Thus, the present invention can be used to measure higher concentration of particles as with other optical schemes.

In a preferred embodiment of the method, multiple photon excitation is used to excite a unit. Multiple photon excitation means that the sum, difference or any other combination of wave frequencies of two, three or more photons is used for excitation of e.g. luminescence. Such an excitation scheme has an advantage in the sense that the excitation probability is not linearly dependent on excitation intensity, but on the second or higher power. Thus, the multiple photon excitation is mostly limited to the volume of the laser focus, whereas outside the laser focus no spurious excitation is generated. The present invention profits from such an excitation scheme in the sense that less background is generated compared to single photon excitation, and that there is no pinhole necessary to restrict the measurement volume. Appropriate laser sources of picosecond or subpicosecond pulses are well known to those of skill in the art.

The nature and the advantages of the invention may be better understood on the basis of the following figures.

FIG. 1. Illustration of the ability of FCS to analyze mixtures. The correlation function G(t) calculated for a mixture of two species having two times different diffusion coefficient is slightly different from G(t) calculated for single species. If the correlation function for a mixture is measured with a sufficient precision, then the analysis yields amplitudes and diffusion times of the terms corresponding to both species.

Figure 2:
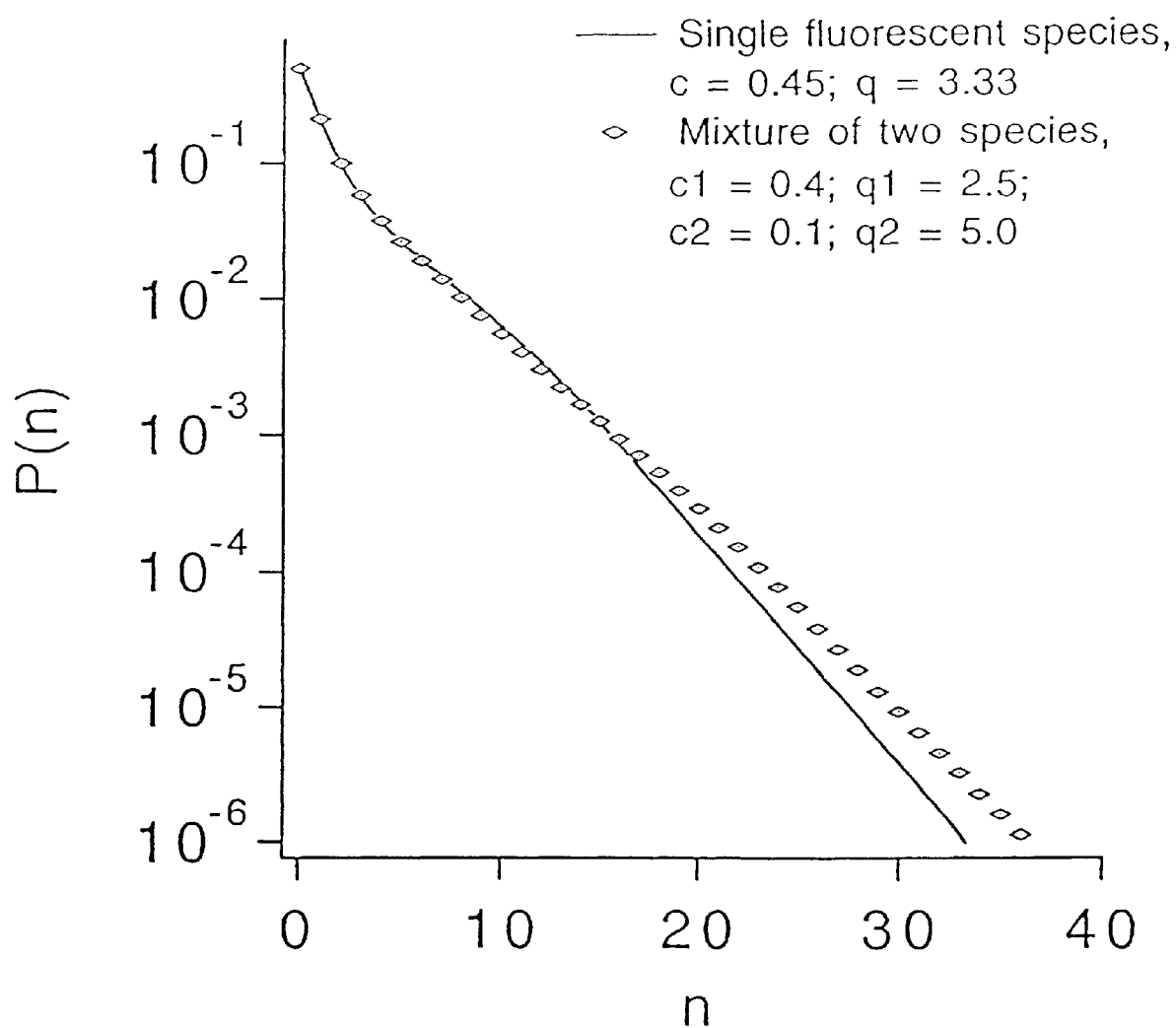
FIG. 2 is a graphic illustration of the ability of FIDA to analyze mixtures as a distribution function of the number of photon counts p(n) calculated for a mixture of two species.

FIG. 2. Illustration of the ability of FIDA to analyze mixtures. The distribution function of the number of photon counts p(n) calculated for a mixture of two species with two times different specific brightness is obviously different from p(n) calculated for single species. Values of concentrations and specific brightnesses are selected to yield equal mean and variance of the count number for both cases. If the distribution function p(n) corresponding to the mixture is accurately measured, then the analysis yields concentrations (number of particles per measurement volume) and specific brightnesses (number of photon counts per particle) of both species.

Figure 3:
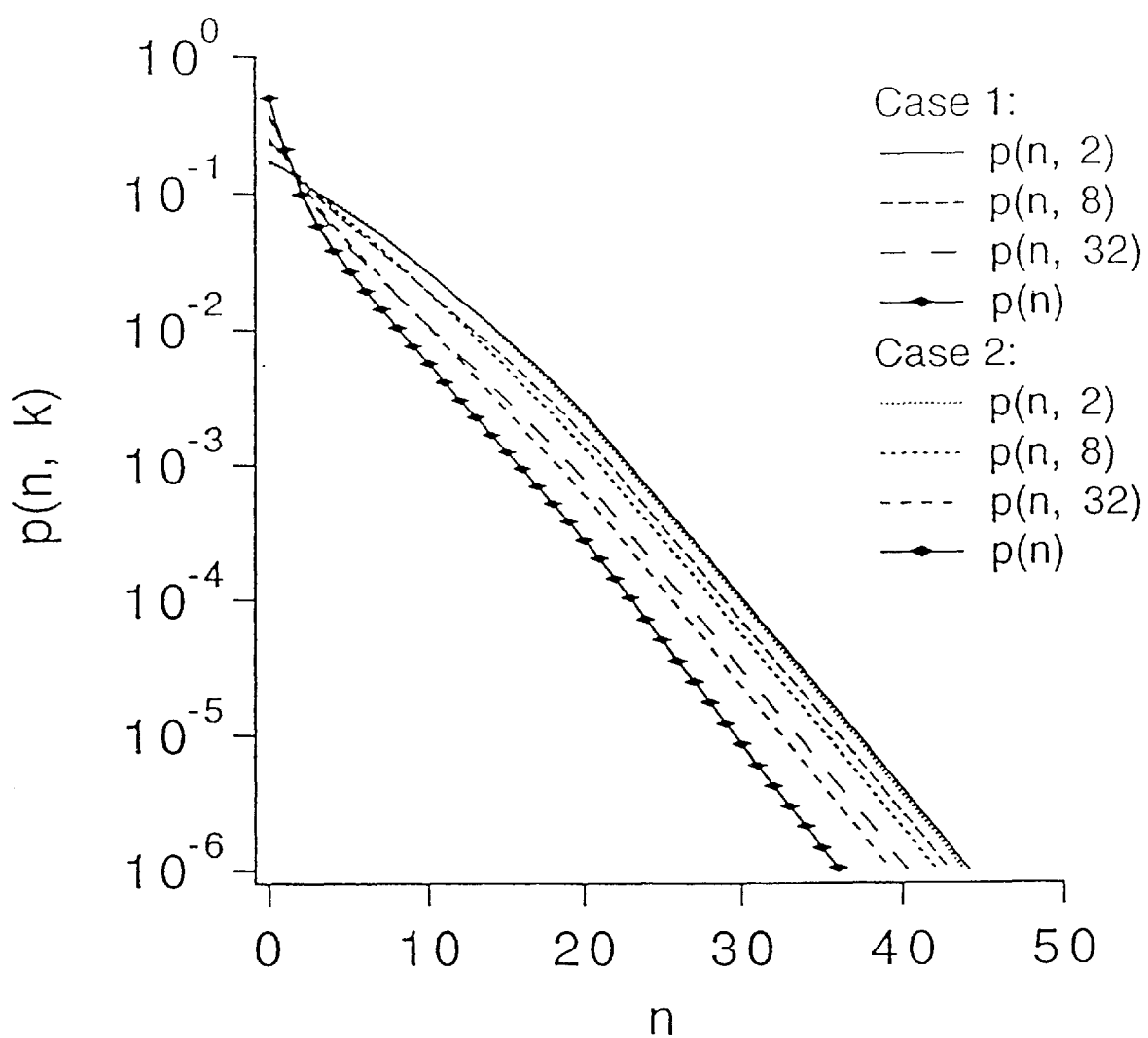
FIG. 3 is a graphic illustration of the ability of the present invention to analyze mixtures as a set of intermediate statistical data, p(n, k), theoretically calculated for two cases which yield identical correlation functions G(t) and distribution functions of photon count number p(n).

FIG. 3. Illustration of the ability of the present invention to analyze mixtures. A set of intermediate statistical data, p(n, k) is theoretically calculated for two cases which yield identical correlation functions G(t) and distribution functions of photon count number p(n), but in case 1 darker particles diffuse two times faster than brighter ones while in case 2 the darker particles are slower. The calculated curves p(n, k) for these two cases differ from each other which means that the present invention can distinguish between the cases which are indistinguishable by both FCS and FIDA.

Figure 4:
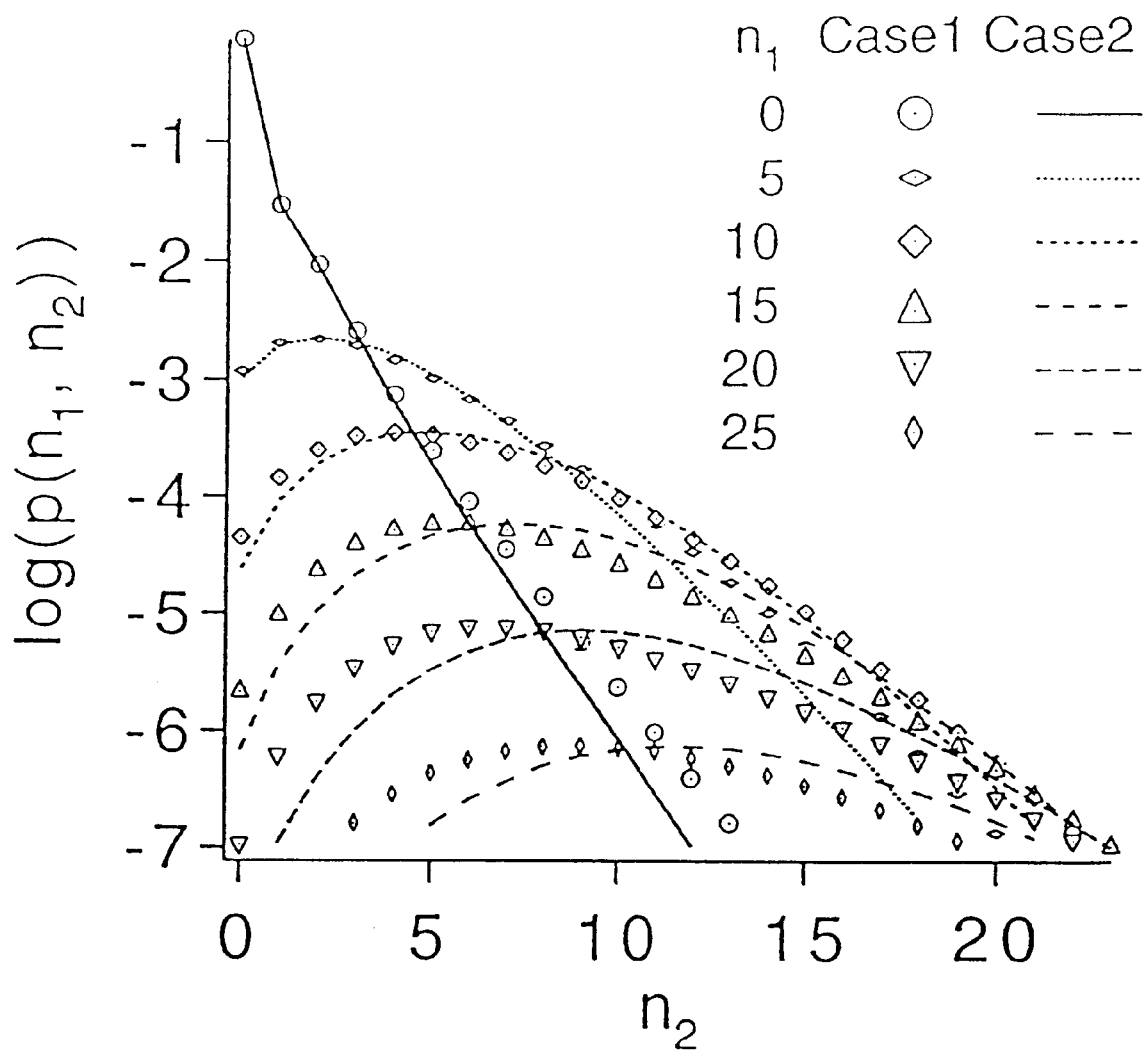
FIG. 4 is a graphic illustration of the ability of the present invention to analyze mixtures of two species as a set of intermediate statistical data, $p(n_1, n_2)$, theoretically calculated for two cases.

FIG. 4. Illustration of the ability of the present invention to analyze mixtures of two species. A set of intermediate statistical data, $p(n_1, n_2)$, is theoretically calculated for two cases. Both cases correspond to mixtures of two fluorescent species. In case 1, fluorescence of one species is polarized: the mean count number per particle is 4.0 for the first and 2.0 for the second detector. Fluorescence of the second species is unpolarized: the mean count number per particle is 3.0 for both detectors. In case 2, fluorescence of both species is moderately polarized: the mean count number per particle is 4.0 and 3.0 for species 1, but 3.0 and 2.0 for species 2. These two cases would yield identical distribution functions of photon count numbers $p(n_1)$ and $p(n_2)$. However, the two-dimensional analysis according to the present invention using $p(n_1, n_2)$ can distinguish case 1 from case 2.

Figure 5:
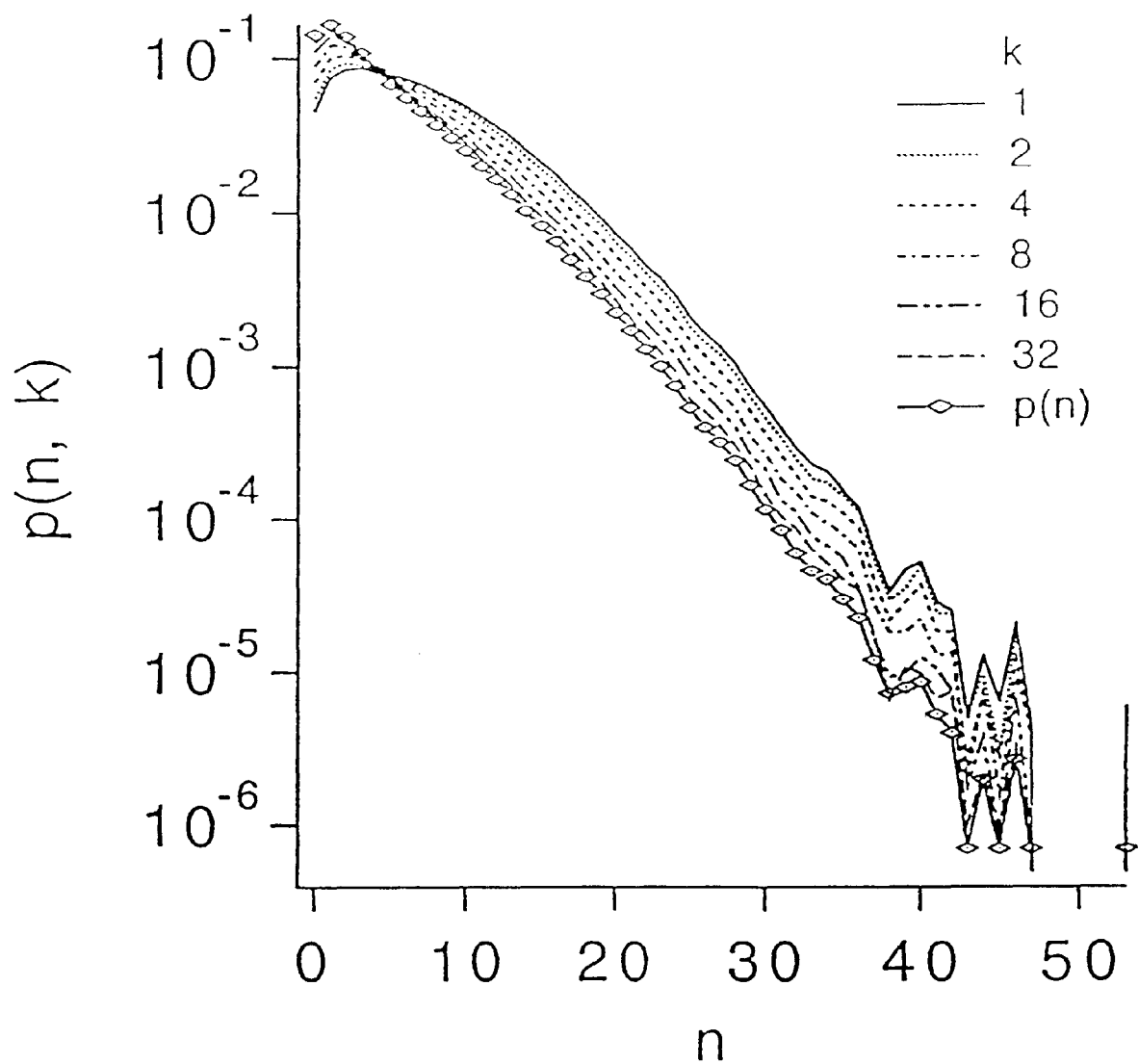
FIG. 5 is a graphic illustration as distributions p(n) and p(n, k) measured for a 0.5 nM tetramethylrhodamine solution in water.

FIG. 5. Distributions p (n) and p(n, k) measured for a 0.5 nM tetramethylrhodamine solution in water. The width of the sampling time window is 40 μs and the data collection time is 60 s.

Figure 6:
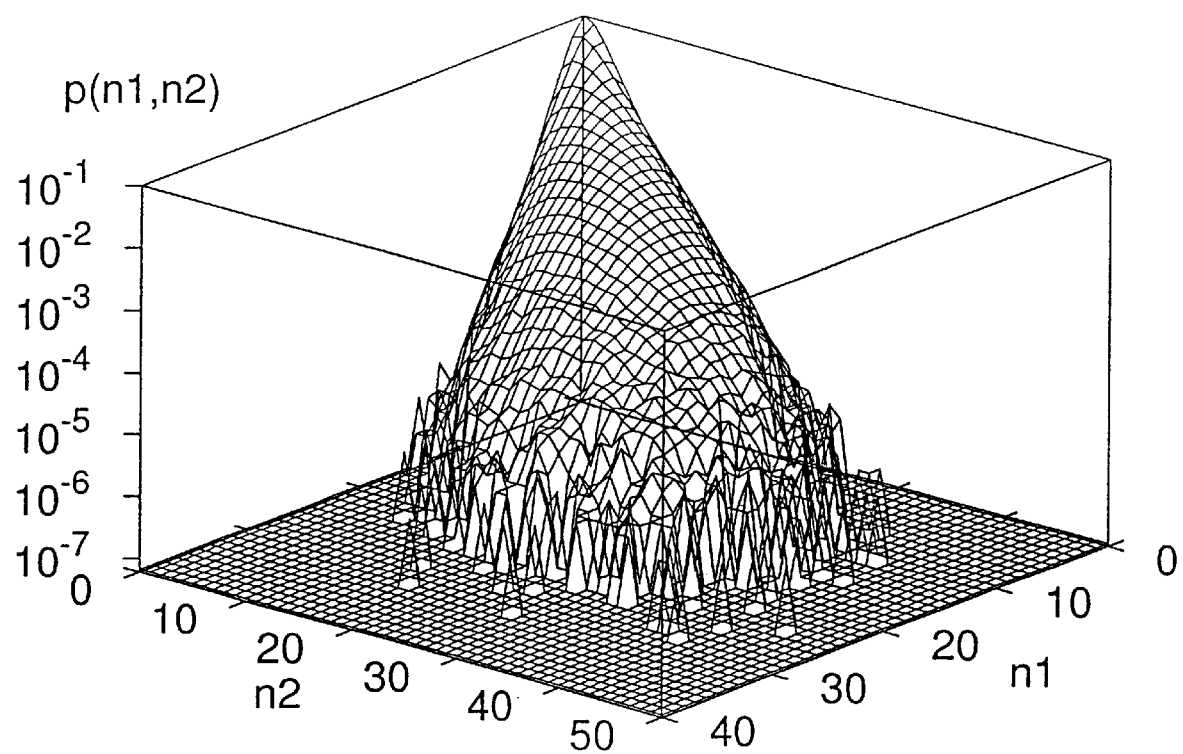
FIGS. 6a, 6b, and 6c are graphic illustrations as distributions p ($n_1, n_2$) measured for aqueous solutions of 1.1 nM tetramethylrhodamine (FIG. 6a), 1.9 nM rhodamine red X (FIG. 6b), and 1.1 nM rhodamine red X (FIG. 6c).
Figure 6:
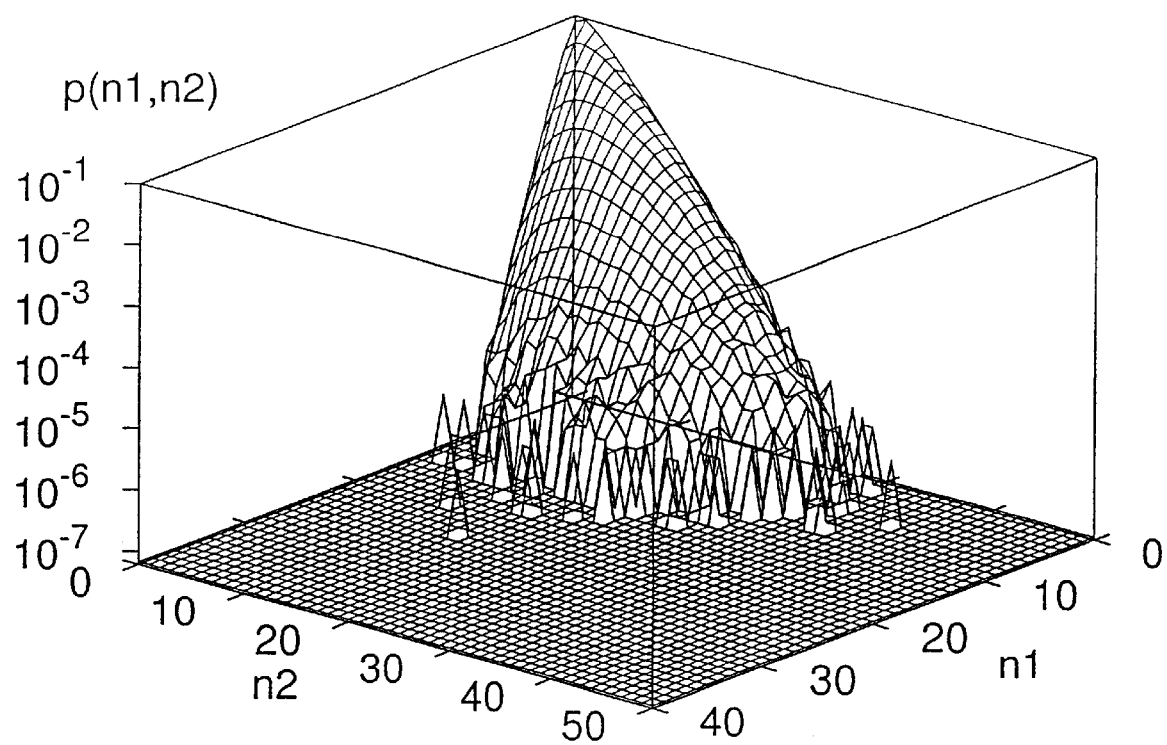
Figure 6:
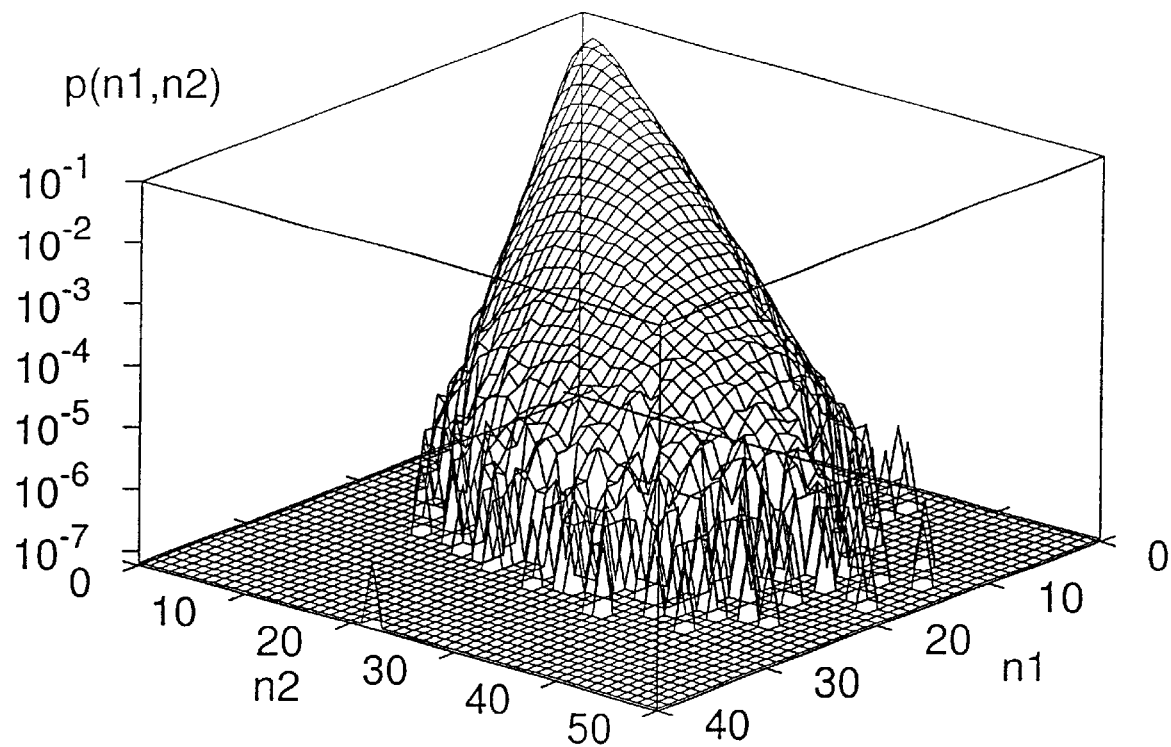

FIG. 6. Distributions p ($n_1$, $n_2$) measured for aqueous solutions of 1.1 nM tetramethylrhodamine (FIG. 6a), 1.9 nM rhodamine red X (FIG. 6b) and 1.1 nM rhodamine red X (FIG. 6c).

Figure 7:
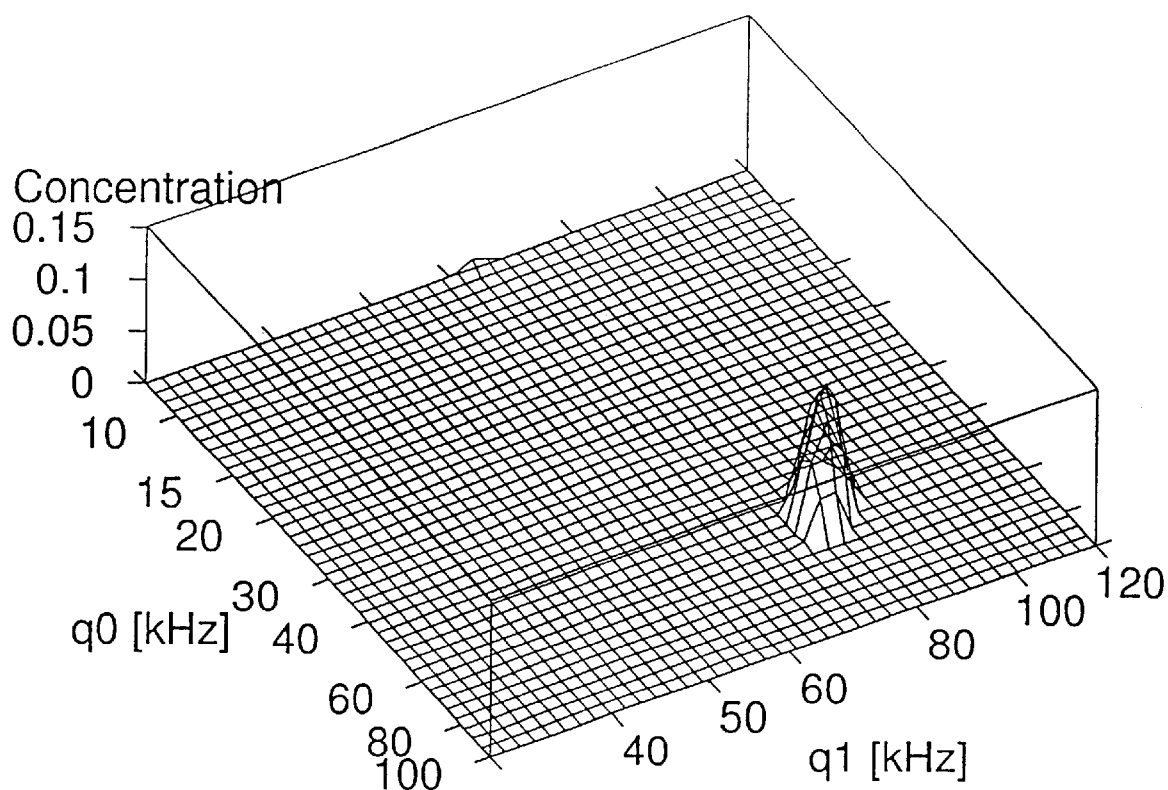
FIGS. 7a, 7b, and 7c are graphic illustrations as distributions c ($q_0, q_1$) determined from experimental data graphed on FIGS. 6a, 6b, and 6c.
Figure 7:
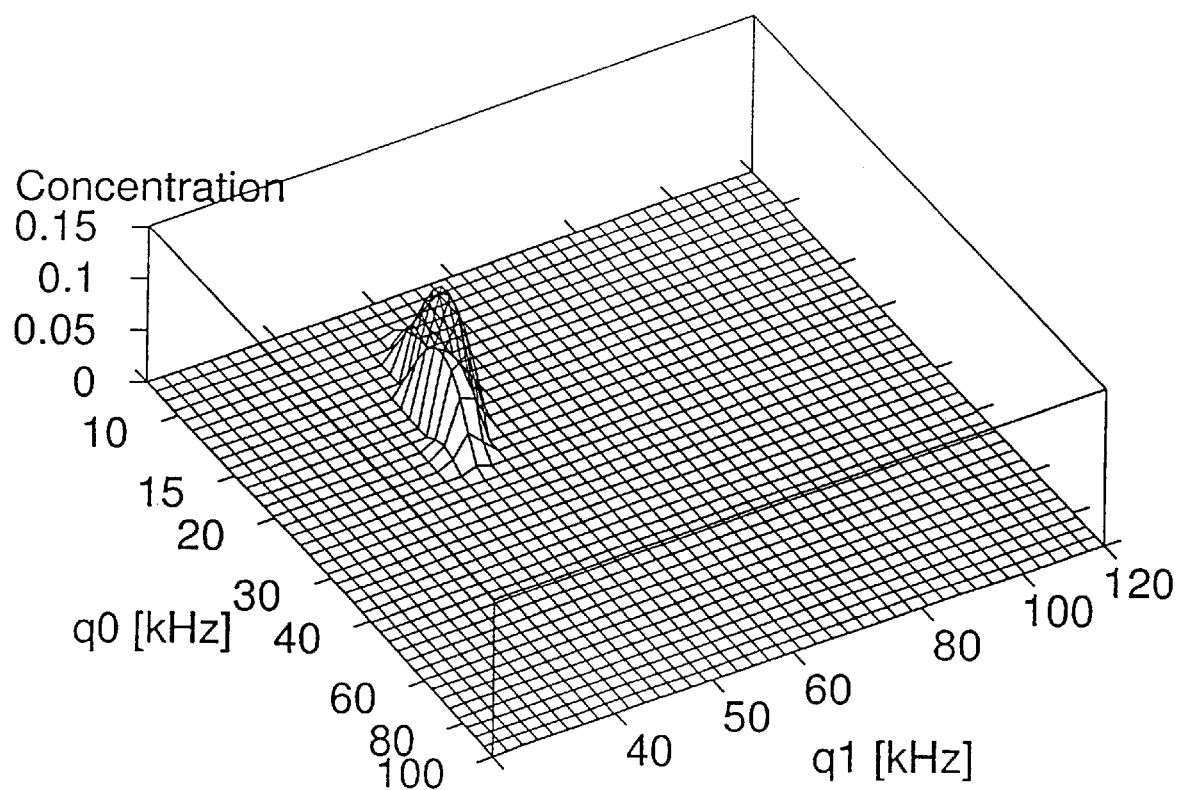
Figure 7:
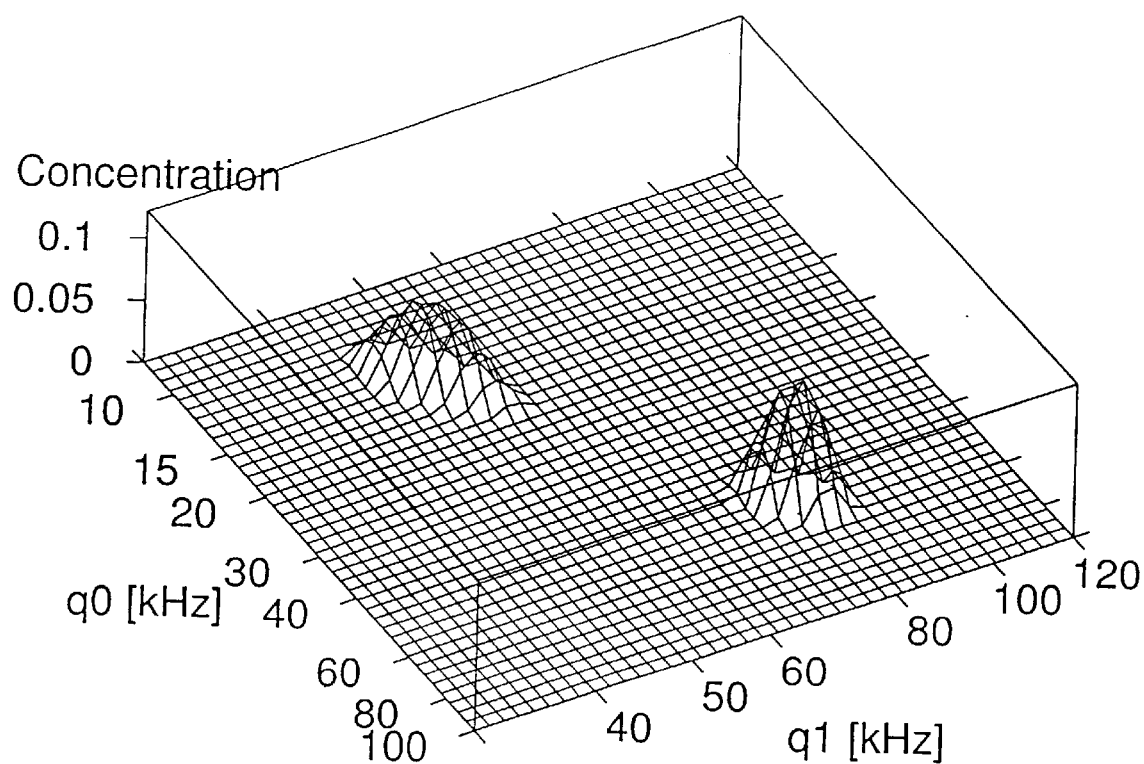

FIG. 7. Distributions c ($q_0$, $q_1$) determined from experimental data graphed on FIG. 6. The distributions (a) and (b) corresponding to single species indeed have a single peak while the distribution (c) has two peaks corresponding to two kinds of molecules.

Figure 8A:
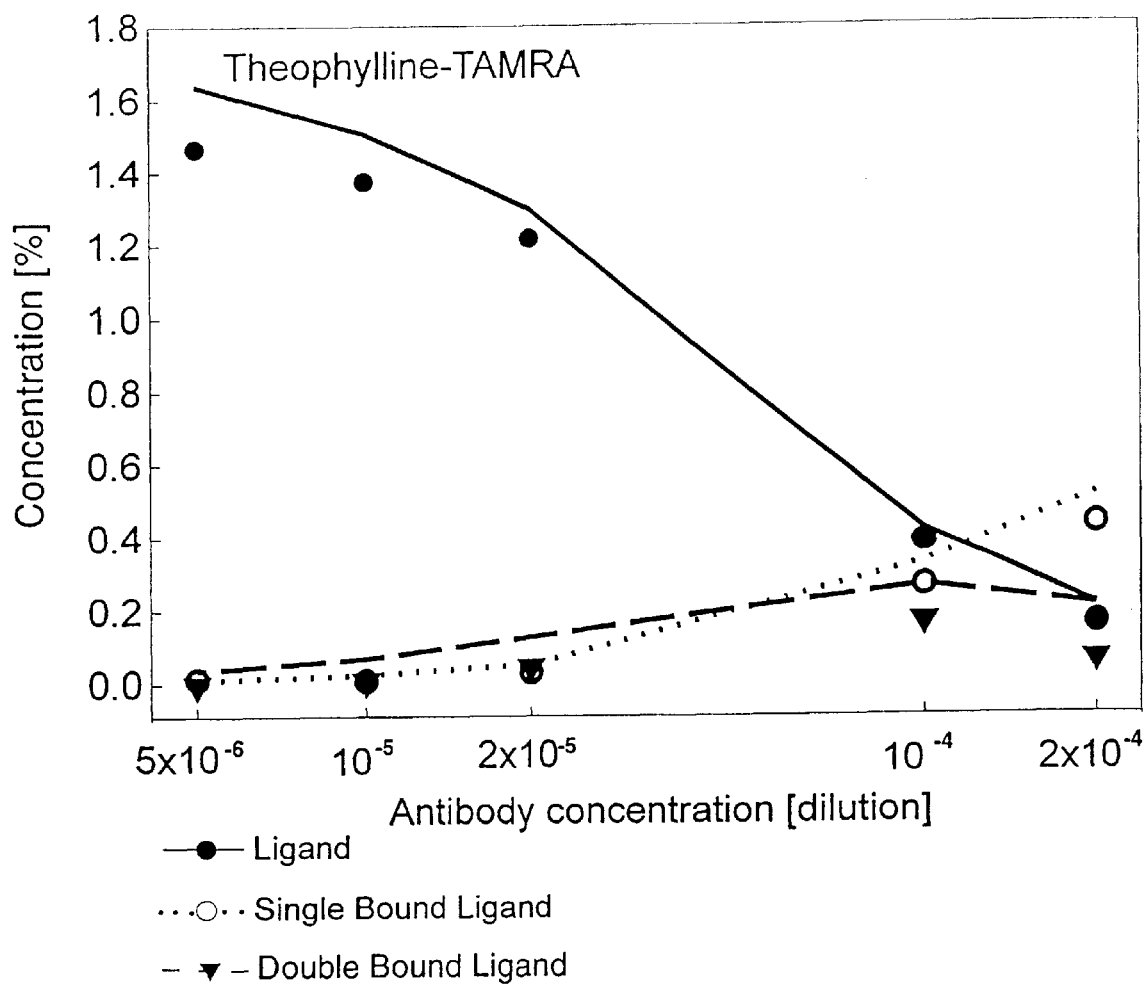
FIGS. 8a and 8b are graphic illustrations of single-species resolution based on multicomponent analysis of global fit alogrithm for the interaction of theophylline-TAMRA (FIG. 8a) and theophylline-spacer-TAMRA (FIG. 8b) with a polyclonal anti-theophylline antibody.
Figure 8B:
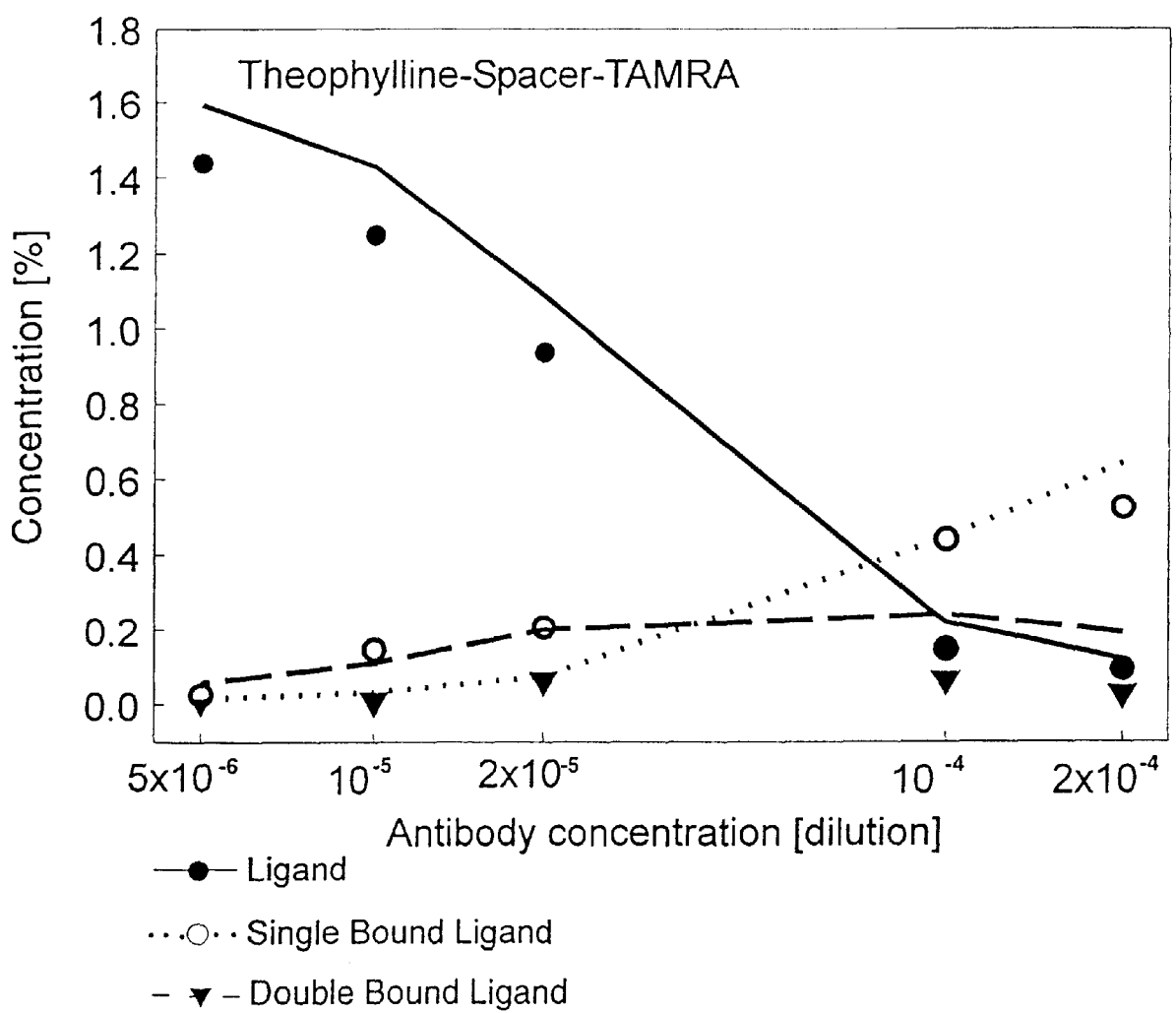

FIG. 8. Single-species resolution based on multicomponent analysis of global fit algorithm for the interaction of theophylline-TAMRA (FIG. 8a) and theophylline-spacer-TAMRA (FIG. 8b) with a polyclonal anti-theophylline antibody. The data were fit according to a model describing two identical and independent binding sites.

EXAMPLE 1

This example represents a two-dimensional combination of FIDA and FCS.

The equipment consists of a confocal microscope (ConfoCor®, Carl Zeiss Jena, Germany) with a water immersion objective (60×, N.A. 1.2), a pinhole in the image plane, a He—Ne-laser of 543 nm emission line, an avalanche photodiode (SPCM-AQ-131, EG&G Optoelectronics, Canada) as a photon detector and a computer with appropriate data acquisition card. The beam was attenuated to about 200 μW at the focus. Emission from samples was optically filtered by a bandpass filter with central wavelength of 580 nm. A sequence of the number of photon counts in consecutive time intervals of given length (20 or 40 μs) was collected as raw data.

From the sequence of the number of counts, denoted as $n_i$ (i=1, ... ,N), the intermediate joint statistical function was determined according to the following formula:

$$P(n, k) = \frac{\sum_{j=k+1}^{N-k} (n_{j-k} + n_{j+k})\delta(n_j, n)}{N - 2k}.$$

wherein k denotes the delay time devided by the width of the counting time interval. The intermediate data determined from experiments were further processed for achieving the best fit with a theoretical model. The theoretical model combines theories of FIDA and FCS. As the outcome of curve fitting, one gets estimated values of concentrations, brightnesses and correlation times of as many species as one assumes to be present.

Five experiments were performed on a 0.5 nM solution of tetramethylrhodamin (TMR, Molecular Probes) in PBS buffer, using the sampling time interval T=20 μs. The duration of each experiment was 40 s. In addition, five further experiments were performed at T=40 μs, using a 0.2 nM solution of TMR. The third set of data files was created semi-artificially, summing pairs of the number of photon counts obtained at T=20 μs and T=40 μs to simulate a mixture of "darker" but "faster" particles with two times "brighter" but "slower" ones. The mixture of fluorescent species with twofold difference in the diffusion time is at the limit of resolution of FCS, whereas a twofold difference of specific brightness is at the limit of resolution of FIDA. The experimentally obtained data were analyzed assuming single species. The semi-artificial data were analyzed assuming two species. The results of analysis are presented in Table 1 below.

EXAMPLE 2

This example illustrates the principle of two-dimensional fluorescence intensity distribution analysis (2D-FIDA).

The equipment is nearly identical to that of example 1, except that fluorescence from the measurement volume is monitored with the help of two photon detectors. In this example, the two detectors differ by transmission spectra of the optical filters: one filter transmits light in the range of 555 to 590 nm while the transmission range of the other filter is 580 to 630 nm. The two specific physical properties characterizing different fluorescent species are count rates per molecule of given species corresponding to the two detection channels. The two-dimensional joint statistical function determined in this example is the (relative) number of events as a function of the number of counts by detectors 1 and 2, $P(n_1,n_2)$. FIG. 6a shows the experimental joint distribution $P(n_1, n_2)$ of a 1.1 nM solution of tetramethyl-rhodamine (TMR, Molecular Probes). Analysis using inverse transform with regularization and constraints (ITRC) yields a single-peak distribution of specific brightnesses, as graphed in FIG. 7a. Similar results are obtained with a solution of another dye, Rhodamine Red X (RRX, Molecular Probes), see FIGS. 6b and 7b. The two samples differ by values of the two specific properties: TMR is characterized by values of 51 and 71.5 kHz/molecule while RRX has values of the same properties of 15.6 and 48. The third sample is a mixture of TMR and RRX solutions, see FIGS. 6c and 7c. As one can notice, two peaks, one corresponding to TMR and the other to RRX, are distinguishable in analysis. This kind of analysis can be used for the determination of concentrations of fluorescent species.

EXAMPLE 3

In this example a case is presented in which only two-dimensional fluorescence intensity distribution analysis (2D-FIDA) yields meaningful results while 1 D-FIDA does not. A binding of two TMR-labelled theophyllines (theophylline-TAMRA and theophylline-spacer-TAMRA (EVOTEC BioSystems GmbH, Germany)) with a polyclonal antitheophylline antibody (Europa Bioproducts, The Netherlands) was studied at different antibody concentrations. All binding studies were performed using the following protocol:

The stock solutions of antibody and antigens are diluted in assay buffer (PBS=phosphate buffered saline +0.05% TWEEN 20, a sorbitan ester. After mixing the compounds, the mixture was incubated for 30 minutes at room temperature. Subsequently, the solution was measured using 1D—and 2D-FIDA approaches. Antibody dilution series were performed at a ligand concentration of 2 nM. All arbitrary antibody concentrations refer to effective dilutions. In FIDA studies the solution was diluted to a single molecule conditions (0.1–1 particle) and rapidly analyzed afer diluting. The system was excited at 543 nm using a 4 mW HE/NE laser (Uniphase, Great Britian). Solutions of TAMR dye and free ligand conjugates were used for alignment of the instrument. All measurements were corrected for water background which was found to be below 1 kHz in each channel.

Reference apparent binding constants ($K_d$) for antibody titration series were determined by fluorescence correlation spectroscopy (FCS) based on a simple one-site binding approximation. In 1 D-FIDA studies two ligand molecules bound to a single antibody molecule appeared as a component with nearly two-fold greater characteristic fluorescence brightness as compared to the free antigen or antibody molecules with a single ligand bound. The brightnesses of the ligand and the single-bound species are similar so that 1D-FIDA cannot be used to determine binding constants for the two-step binding.

In 2D-FIDA experiments, by the application of a FIT-mode procedure, individual species were separated, signals classified, and $K_d$'s were compared with FCS binding data using a model which assumes the existence of two identical, but independent binding sites:

$$R + L \rightleftharpoons RL \quad K_d = \frac{[R][L]}{[RL]}$$

$$RL + L \rightleftharpoons RL_2 \quad K_d = \frac{[RL][L]}{[RL_2]}$$

where L is the ligand and R the antibody with two binding sites. The following mass relations are valid:

$$[L]=[L_0]-[RL]-2[RL_2]$$

$$[R]=[R_0]+[RL]-[RL_2]$$

The model was simulated and fit using MATHCAD (MathSoft, US) and SCIENTIST (MicroMath, US) software packages. 2D-FIDA could distinguish (at least) three species with different brightnesses and their concentrations as determined from global fit analysis. Using 2D-FIDA, the appearance of intermediates can be demonstrated very easily illustrated by examining the concentration of the doubly-bound ligand at different antibody concentrations (FIGS. 8a, b).

The experimental data are in good agreement with simulations according to the model considering two identical and independent binding sites. Fitting of the data sets leads to binding constants which are consistent with brightness corrected FCS data for the different antigens used.

What is claimed is:

1. A method for characterizing samples which contain fluorescent molecules or particles, comprising the steps of:
   a) monitoring a sample for intensity fluctuations of radiation emitted by the molecules or particles in at least one measurement volume by detecting sequences of photon counts by a single, two or more photon detectors,
   b) determining, from said sequences of photon counts, intermediate statistical data, said intermediate statistical data comprising a probability function of at least two arguments, wherein at least one of the arguments is a number of photon counts $n_1$ counted by detector 1 and another argument is a number of photon counts $n_2$ counted by detector 2,
   c) determining a distribution of molecules or particles as a function of at least two specific physical properties out of said intermediate statistical data.

2. The method according to claim 1, wherein the probability function expresses the probability to count n photons in the k-th time interval provided an occasional photon was counted in the 0-th time interval and k denotes the time delay divided by the width of the counting interval.

3. The method according to one of claim 2, wherein said molecules or particles can be grouped into species which can be distinguished by at least one of their specific physical properties.

4. The method according to one of claim 2, wherein in step c) the presence or absence or concentration of at least one species of molecules or particles with a specific combination of at least two physical properties is determined.

5. The method according to one of claim 2, wherein said intermediate statistical data additionally comprise statistical functions of a single argument.

6. The method according to one of claim 2, wherein the sample contains aggregates, vesicles, cells, viruses, bacteria, beads, centers or mixtures thereof in solids, liquids or gases.

7. The method according to one of claim 2, wherein at least one of the specific physical properties characterizing said molecules or particles is the diffusion coefficient, or correlation time of radiation intensity fluctuations, or any other property directly related to said diffusion coefficient.

8. The method according to one claim 2, wherein at least one of the specific physical properties characterizing said molecules or particles is their ability to emit, scatter or reflect radiation.

9. The method according to one of claim 2, wherein at least one of the specific physical properties characterizing said molecules or particles expresses the property of said molecules or particles to emit polarized fluorescence.

10. The method according to one of claim 2, wherein at least one of the specific physical properties characterizing said molecules or particles is the ratio of fluorescence intensities corresponding to different excitation wavelengths, or different spectral sensitivities of fluorescence detection, or any other property expressing the dependence of fluorescence intensity on either the wavelength of excitation or detection, or on both wavelengths.

11. The method according to one of claim 2, wherein at least one of the specific physical properties characterizing said molecules or particles is lifetime of fluorescence.

12. The method according to one of claim 2, wherein the specific physical properties of the molecules or particles are varied by conjugating them with a specific luminophore via different linker molecules.

13. The method according to claim 12, wherein the specific physical properties are luminescence properties.

14. The method according to claim 13, wherein the luminescence properties are fluorescence lifetime or fluorescence anistropy.

15. The method according to one of claim 2, wherein the luminescence properties of the molecules or particles are changed by energy transfer, in which energy absorbed by the molecule or particle is transferred upon close contact to a luminophore of an acceptor molecule or particle and subsequently emitted.

16. The method according to one of claim 2, wherein said intermediate statistical data are fitted using a priori information on the sample.

17. The method according to one of claim 2, wherein said statistical data are processed applying multidimensional inverse transformation with linear regularization, multidimensional inverse transformation with constraints, or multidimensional inverse transformation with both linear regularization and constraints.

18. The method according to one of claim 2, wherein the measurement volume is only a part of the total volume of the sample and has a volume $\leq 10^{-12}$ l.

19. The method according to claim 18, wherein the measurement volume has a volume $\leq 10^{-14}$ l.

20. The method according to one of claim 2 using at least one microscope objective in a confocal manner for focusing an incident laser beam and collecting radiation emitted, scattered or reflected by molecules or particles in the sample.

21. The method according to claim 20 using at least one microscope objective with a numerical aperture $\geq 0.9$.

22. The method according to one of claim 2, wherein the measurement volume is restricted by the use of elements of near field spectroscopy.

23. The method according to one of claim 2, wherein multiple photon excitation is used to excite said molecules or particles.

24. The method according to claim 1, wherein said molecules or particles can be grouped into species which can be distinguished by at least one of their specific physical properties.

25. The method according to claim 1, wherein in step c) the presence or absence or concentration of at least one species of molecules or particles with a specific combination of at least two physical properties is determined.

26. The method according to claim 1, wherein said intermediate statistical data additionally comprise statistical functions of a single argument.

27. The method according to claim 1, wherein the sample contains aggregates, vesicles, cells, viruses, bacteria, beads, centers or mixtures thereof in solids, liquids or gases.

28. The method according to claim 1, wherein at least one of the specific physical properties characterizing said molecules or particles is the diffusion coefficient, or correlation time of radiation intensity fluctuations, or any other property directly related to said diffusion coefficient.

29. The method according to claim 1, wherein at least one of the specific physical properties characterizing said molecules or particles is their ability to emit, scatter or reflect radiation.

30. The method according to claim 1, wherein at least one of the specific physical properties characterizing said molecules or particles expresses the property of said molecules or particles to emit polarized fluorescence.

31. The method according to claim 1, wherein at least one of the specific physical properties characterizing said molecules or particles is the ratio of fluorescence intensities corresponding to different excitation wavelengths, or different spectral sensitivities of fluorescence detection, or any other property expressing the dependence of fluorescence intensity on either the wavelength of excitation or detection, or on both wavelengths.

32. The method according to claim 1, wherein at least one of the specific physical properties characterizing said molecules or particles is lifetime of fluorescence.

33. The method according to claim 1, wherein the specific physical properties of the molecules or particles are varied by conjugating them with a specific luminophore via different linker molecules.

34. The method according to claim 33, wherein the specific physical properties are luminescence properties.

35. The method according to claim 34, wherein the luminescence properties are fluorescence lifetime or fluorescence anisotropy.

36. The method according to claim 1, wherein the luminescence properties of the molecules or particles are changed by energy transfer, in which energy absorbed by the molecule or particle is transferred upon close contact to a luminophore of an acceptor molecule or particle and subsequently emitted.

37. The method according to claim 1, wherein said intermediate statistical data are fitted using a priori information on the sample.

38. The method according to claim 1, wherein said statistical data are processed applying multidimensional inverse transformation with linear regularization, multidimensional inverse transformation with constraints, or multidimensional inverse transformation with both linear regularization and constraints.

39. The method according to claim 1, wherein the measurement volume is only a part of the total volume of the sample and has a volume $\leq 10^{-12}$ l.

40. The method according to claim 44, wherein the measurement volume has a volume $\leq 10^{-14}$ l.

41. The method according to claim 1 using at least one microscope objective in a confocal manner for focusing an incident laser beam and collecting radiation emitted, scattered or reflected by molecules or particles in the sample.

42. The method according to claim 41 using at least one microscope objective with a numerical aperture $\geq 0.9$.

43. The method according to claim 1, wherein the measurement volume is restricted by the use of elements of near field spectroscopy.

44. The method according to claim 1, wherein multiple photon excitation is used to excite said molecules or particles.

45. A method for characterizing samples which contain fluorescent molecules or particles, comprising the steps of:
  a) monitoring a sample for intensity fluctuations of radiation emitted by the molecules or particles in at least one measurement volume by detecting sequences of photon counts by a single, two or more photon detectors,
  b) determining, from said sequences of photon counts, intermediate statistical data, said intermediate statistical data comprising a probability function of at least two arguments, wherein at least one of the arguments is a number of photon counts and another is a width of a counting time interval,
  c) determining a distribution of molecules or particles as a function of at least two specific physical properties out of said intermediate statistical data.

46. The method according to claim 45, wherein said molecules or particles can be grouped into species which can be distinguished by at least one of their specific physical properties.

47. The method according to claim 45, wherein in step c) the presence or absence or concentration of at least one species of molecules or particles with a specific combination of at least two physical properties is determined.

48. The method according to claim 45, wherein said intermediate statistical data additionally comprise statistical functions of a single argument.

49. The method according to claim 45, wherein the sample contains aggregates, vesicles, cells, viruses, bacteria, beads, centers or mixtures thereof in solids, liquids or gases.

50. The method according to claim 45, wherein at least one of the specific physical properties characterizing said molecules or particles is the diffusion coefficient, or correlation time of radiation intensity fluctuations, or any other property directly related to said diffusion coefficient.

51. The method according to claim 45, wherein at least one of the specific physical properties characterizing said molecules or particles is their ability to emit, scatter or reflect radiation.

52. The method according to claim 45, wherein at least one of the specific physical properties characterizing said molecules or particles expresses the property of said molecules or particles to emit polarized fluorescence.

53. The method according to claim 45, wherein at least one of the specific physical properties characterizing said molecules or particles is the ratio of fluorescence intensities corresponding to different excitation wavelengths, or different spectral sensitivities of fluorescence detection, or any other property expressing the dependence of fluorescence intensity on either the wavelength of excitation or detection, or on both wavelengths.

54. The method according to claim 45, wherein at least one of the specific physical properties characterizing said molecules or particles is lifetime of fluorescence.

55. The method according to claim 45, wherein the specific physical properties of the molecules or particles are varied by conjugating them with a specific luminophore via different linker molecules.

56. The method according to claim 55, wherein the specific physical properties are luminescence properties.

57. The method according to claim 56, wherein the luminescence properties are fluorescence lifetime or fluorescence anistropy.

58. The method according to claim 45, wherein the luminescence properties of the molecules or particles are changed by energy transfer, in which energy absorbed by the molecule or particle is transferred upon close contact to a luminophore of an acceptor molecule or particle and subsequently emitted.

59. The method according to claim 45, wherein said intermediate statistical data are fitted using a priori information on the sample.

60. The method according to claim 45, wherein said statistical data are processed applying multidimensional inverse transformation with linear regularization, multidimensional inverse transformation with constraints, or multidimensional inverse transformation with both linear regularization and constraints.

61. The method according to claim 45, wherein the measurement volume is only a part of the total volume of the sample and has a volume $\leq 10^{-12}$ l.

62. The method according to claim 61, wherein the measurement volume has a volume $\leq 10^{-14}$ l.

63. The method according to claim 45 using at least one microscope objective in a confocal manner for focusing an incident laser beam and collecting radiation emitted, scattered or reflected by molecules or particles in the sample.

64. The method according to claim 63 using at least one microscope objective with a numerical aperture $\geq 0.9$.

65. The method according to claim 45, wherein the measurement volume is restricted by the use of elements of near field spectroscopy.

66. The method according to claim 45, wherein multiple photon excitation is used to excite said molecules or particles.

67. A method for characterizing samples which contain fluorescent molecules or particles, comprising the steps of:
a) monitoring a sample for intensity fluctuations of radiation emitted by the molecules or particles in at least one measurement volume by detecting sequences of photon counts by a single, two or more photon detectors,
b) determining, from said sequences of photon counts, intermediate statistical data, said intermediate statistical data comprising a probability function of at least two arguments, wherein at least one of the arguments is a number of photon counts and another is a time delay from an incident count,
c) determining a distribution of molecules or particles as a function of at least two specific physical properties out of said intermediate statistical data.

68. A method for characterizing samples which contain fluorescent molecules or particles, comprising the steps of:
a) monitoring a sample for intensity fluctuations of radiation emitted by the molecules or particles in at least one measurement volume by detecting sequences of photon counts by a single, two or more photon detectors,
b) determining, from said sequences of photon counts, intermediate statistical data comprising a probability function of at least two arguments, wherein at least one of the arguments is number of photon counts and another is a length of time intervals between consecutive photon counts,
c) determining a distribution of molecules or particles as a function of at least two specific physical properties out of said intermediate statistical data.

69. The method according to claim 68, wherein said molecules or particles can be grouped into species which can be distinguished by at least one of their specific physical properties.

70. The method according to claim 68, wherein in step c) the presence or absence or concentration of at least one species of molecules or particles with a specific combination of at least two physical properties is determined.

71. The method according to claim 68, wherein said intermediate statistical data additionally comprise statistical functions of a single argument.

72. The method according to claim 68, wherein the sample contains aggregates, vesicles, cells, viruses, bacteria, beads, centers or mixtures thereof in solids, liquids or gases.

73. The method according to claim 68, wherein at least one of the specific physical properties characterizing said molecules (r particles is the diffusion coefficient, or correlation time of radiation intensity fluctuations, or any other property directly related to said diffusion coefficient.

74. The method according claim 68, wherein at least one of the specific physical properties characterizing said molecules or particles is their ability to emit, scatter or reflect radiation.

75. The method according to claim 68, wherein at least one of the specific physical properties characterizing said molecules or particles expresses the property of said molecules or particles to emit polarized fluorescence.

76. The method according to claim 68, wherein at least one of the specific physical properties characterizing said molecules or particles is the ratio of fluorescence intensities corresponding to different excitation wavelengths, or different spectral sensitivities of fluorescence detection, or any other property expressing the dependence of fluorescence intensity on either the wavelength of excitation or detection, or on both wavelengths.

77. The method according to claim 68, wherein at least one of the specific physical properties characterizing said molecules or particles is lifetime of fluorescence.

78. The method according to claim 68, wherein the specific physical properties of the molecules or particles are varied by conjugating them with a specific luminophore via different linker molecules.

79. The method according to claim 78, wherein the specific physical properties are luminescence properties.

80. The method according to claim 79 wherein the luminescence properties are fluorescence lifetime or fluorescence anistropy.

81. The method according to claim 68, wherein the luminescence properties of the molecules or particles are changed by energy transfer, in which energy absorbed by the molecule or particle is transferred upon close contact to a luminophore of an acceptor molecule or particle and subsequently emitted.

82. The method according to claim 68, wherein said intermediate statistical data are fitted using a priority information on the sample.

83. The method according to claim 68, wherein said statistical data are processed applying multidimensional inverse transformation with linear regularization, multidimensional inverse transformation with constraints, or multidimensional inverse transformation with both linear regularization and constraints.

84. The method according to claim 68, wherein the measurement volume is only a part of the total volume of the sample and has a volume $\leq 10^{-12}$ l.

85. The method according to claim 84, wherein the measurement volume has a volume $\leq 10^{-14}$ l.

86. The method according to claim 68 using at least one microscope objective in a confocal manner for focusing an incident laser beam and collecting radiation emitted, scattered or reflected by molecules or particles in the sample.

87. The method according to claim 86 using at least one microscope objective with a numerical aperture $\geq 0.9$.

88. The method according to claim 68, wherein the measurement volume is restricted by the use of elements of near field spectroscopy.

89. The method according to claim 68, wherein multiple photon excitation is used to excite said molecules or particles.

* * * * *